US012688927B2

(12) United States Patent
Chen et al.

(10) Patent No.: US 12,688,927 B2
(45) Date of Patent: Jul. 21, 2026

(54) IMAGE FEATURE CLASSIFICATION

(71) Applicant: KONINKLIJKE PHILIPS N.V.,
Eindhoven (NL)

(72) Inventors: Hongxin Chen, Shanghai (CN); Jiayin Zhou, Eindhoven (NL); Sa Yuan Liang, Eindhoven (NL); Yi Fan, Eindhoven (NL)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 313 days.

(21) Appl. No.: 18/038,112

(22) PCT Filed: Nov. 23, 2021

(86) PCT No.: PCT/EP2021/082581

§ 371 (c)(1),
(2) Date: May 22, 2023

(87) PCT Pub. No.: WO2022/112201

PCT Pub. Date: Jun. 2, 2022

(65) Prior Publication Data

US 2023/0360776 A1 Nov. 9, 2023

(30) Foreign Application Priority Data

Nov. 24, 2020 (WO) ................ PCT/CN2020/131090
Feb. 24, 2021 (EP) .................................... 21159015

(51) Int. Cl.
*G16H 30/40* (2018.01)
*G06V 10/80* (2022.01)
*G06V 10/82* (2022.01)

(52) U.S. Cl.
CPC ............. *G16H 30/40* (2018.01); *G06V 10/80* (2022.01); *G06V 10/82* (2022.01); *G06V 2201/031* (2022.01); *G06V 2201/032* (2022.01)

(58) Field of Classification Search
None
See application file for complete search history.

(56) References Cited

U.S. PATENT DOCUMENTS 10,496,884 B1 * 12/2019 Nguyen ............... G06N 3/0464
2006/0052690 A1 * 3/2006 Sirohey .................. A61B 6/481
600/420

(Continued)

FOREIGN PATENT DOCUMENTS

CN 107622485 A 1/2018
EP 3150125 A1 4/2017
EP 3150125 B1 * 3/2021 ............. A61B 6/481

OTHER PUBLICATIONS

Zhou et al., "A Deep Learning-Based Radiomics Model for Differentiating Benign and Malignant Renal Tumors," Translational Oncology, vol. 12, No. 2, Feb. 2019, pp. 292-300 (Year: 2019).*

(Continued)

*Primary Examiner* — Soo Shin

(57) ABSTRACT

A method and system for image feature classification using a NN-based learning algorithms to make a decision about a feature in a medical image or image part. In particular, embodiments may make use of a phase of a multi-phasic image to improve classification accuracy. For instance, embodiments may combine different phases of multiphasic images as training data.

20 Claims, 8 Drawing Sheets

(56)  References Cited

U.S. PATENT DOCUMENTS

| 2011/0002520 A1* | 1/2011 | Suehling | G06T 7/0012 |
| | | | 382/154 |
| 2018/0276817 A1* | 9/2018 | Isgum | G06T 7/10 |
| 2019/0205606 A1* | 7/2019 | Zhou | G06N 3/045 |
| 2019/0318476 A1* | 10/2019 | Isgum | G16H 50/20 |
| 2021/0233645 A1* | 7/2021 | Morard | G06T 7/174 |
| 2022/0343638 A1* | 10/2022 | Wang | G16H 30/40 |

OTHER PUBLICATIONS

Zhen et al., "Deep Learning for Accurate Diagnosis of Liver Tumor Based on Magnetic Resonance Imaging and Clinical Data", Frontiers in Oncology, vol. 10, Article 680, May 2, 20208, pp. 1-14.

Hamm et al., "Deep learning for liver tumor diagnosis part I: development of a convolutional neural network classifier for multiphasic MRI", European Radiology (2019) 29, pp. 3338-3347.

Wang et al., "Deep learning for liver tumor diagnosis part II: development of a convolutional neural network classifier for multiphasic MRI", European Radiology (2019) 29:3348-3357.

International Search report and Written Opinion of PCT/EP2021/082581, dated Mar. 10, 2022.

* cited by examiner second channel

| $i \cdot c$ | $i \cdot c$ | $i \cdot c$ | ... |
|---|---|---|---|

| | $a_{00}$ | $a_{01}$ | $a_{02}$ | ... |
|---|---|---|---|---|
| $i \cdot c$ | | | | |
| $i \cdot c$ | $a_{10}$ | ... | ... | ... |
| $i \cdot c$ | $a_{20}$ | ... | ... | ... |
| ... | ... | ... | ... | ... | phase ID: i
(0/1/2)

first channel

| Obtaining a medical image and a phase identifier associated with the medical image | 610 |

| Combine the medical image and the phase identifier to generate modified image data | 620 |

| Provide modified image data as an input of a layer of a NN-based learning algorithm | 630 |

| Obtain an image feature classification result from the NN-based learning algorithm | 640 |

700

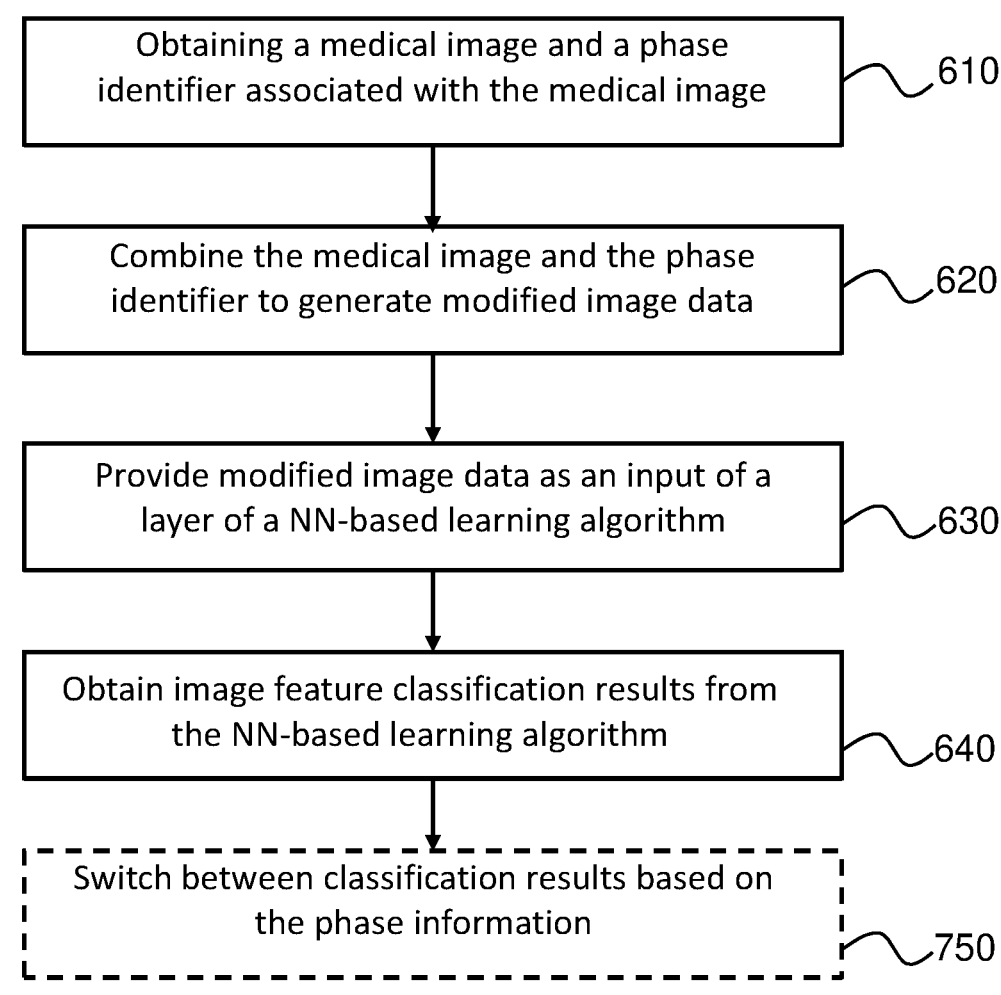

| Obtaining a medical image and a phase identifier associated with the medical image | 610 |

| Combine the medical image and the phase identifier to generate modified image data | 620 |

| Provide modified image data as an input of a layer of a NN-based learning algorithm | 630 |

| Obtain image feature classification results from the NN-based learning algorithm | 640 |

| Switch between classification results based on the phase information | 750 |

FIG. 7

IMAGE FEATURE CLASSIFICATION

CROSS-REFERENCE TO PRIOR APPLICATIONS

This application is the U.S. National Phase application under 35 U.S.C. § 371 of International Application No. PCT/EP2021/082581, filed on Nov. 23, 2021, which claims the benefit of International Application No. PCT/CN2020/131090 filed on Nov. 24, 2020 and European Patent Application No. 21159015.3, filed on Feb. 24, 2021. These applications are hereby incorporated by reference herein.

FIELD OF THE INVENTION

The invention relates to the field of image feature classification, and in particular to classifying image features of multi-phasic medical images.

BACKGROUND OF THE INVENTION

Rapid and reliable detection and diagnosis of medical image features (such as lesions or tumours) may allow for earlier treatment onset and better outcomes for subjects (i.e. patients). As the availability and quality of medical imaging have improved, the need for invasive diagnostic biopsies has decreased, propelling imaging-based diagnosis to a more central role, with a unique status especially for primary liver cancer. However, the radiological diagnosis of potentially malignant hepatic lesions remains a challenging task. For example, enhancement washout or capsule features of medical images are very important, but, because their presence in medical image is typically decided manually (e.g. by a physician), the decision process may be inefficient and/or may result in different decision results across physicians with different expertise or experience.

Standardized image analysis and reporting frameworks have therefore been developed to improve radiological diagnosis by reducing imaging interpretation variability, improving communication with referring physicians, and facilitating quality assurance and research. A prominent example of such a reporting framework is the Liver Imaging Reporting and Data System (LI-RADS) framework for standardizing the reporting and data collection of CT and MR imaging for hepatocellular carcinoma (HCC).

However, the increasing complexity of such reporting frameworks have made implementation less feasible in a high-volume practice, leaving an unmet clinical need for computational decision-support tools to improve workflow efficiency. There is therefore a need for a classification assistance system that may be integrated into a clinical workflow to provide physicians with information that will enable them to classify features of multi-phasic medical images more efficiently and with improved confidence.

SUMMARY OF THE INVENTION

The invention is defined by the claims.

According to examples in accordance with an aspect of the invention, there is provided a computer-implemented method for classifying image features of multi-phasic medical images. The method comprises: obtaining a medical image and a phase identifier associated with the medical image, the phase identifier representing the phase of the image; combining the medical image and the phase identifier to generate modified image data; providing the modified image data as an input of a layer of a Neural Network, NN-based learning algorithm configured to classify image features; and obtaining, for the modified image data, an image feature classification result from the NN-based learning algorithm.

Proposed embodiments provide image feature classification using a NN-based learning algorithms to make a decision about a feature in a medical image or image part (e.g. which includes a lesion). In particular, embodiments may make use of a phase of a multi-phasic image to improve classification accuracy. For instance, embodiments may combine different phases of multiphasic images as training data.

The NN-based learning algorithm may be trained using a training algorithm configured to receive an array of training inputs and known outputs, wherein the training inputs comprise medical image, medical image segments or medical image features, and wherein the known outputs comprise image feature classifications. In this way, the NN-based learning algorithms may be trained to output an image feature classification when provided with a medical image and a phase identifier associated with the medical image. That is image data and phase data may be combined and, in this way, image data for different phases can be leveraged together for improved training and classification.

The medical image may, for example, comprise an image of at least a portion of a liver. The NN-based learning algorithm may then comprise a Liver Imaging Reporting and Data System, LI-RADS, feature classifier trained to make a decision about the classification of an image feature.

In some embodiments, combining the medical image and the phase identifier may comprise: processing the image with an image feature generation algorithm to generate a tensor representing one or more features of the image; and combining the phase identifier with tensor to generate, as the modified image data, a modified tensor. The process of providing the modified image data to a layer of the NN-based learning algorithm may then comprise providing the modified tensor to a hidden layer trained to make a decision about the classification of an image feature.

By way of example, the hidden layer of the NN may include one layer of the convolution or one layer of the fully connection.

In an embodiment, combining the medical image and the phase identifier may comprise modifying data of the image based on the phase identifier to generate modified image data. For example, modifying the data of the image may comprise concatenating the phase identifier to the image as an extract channel. In another example, the phase identifier may comprise a numerical value, and modifying the data of the image may then comprises at last one of: adding the numerical value of the phase identifier to pixel values of the image; and multiplying pixel values of the image by the numerical value of the phase identifier. Simple mathematical operations may therefore be employed by embodiments, thus minimizing cost and/or complexity of implementation.

In some embodiment, obtaining, for the modified image data, an image feature classification result from the NN-based learning algorithm may comprise: obtaining a plurality of image feature classification results from the NN-based learning algorithm; and switching between the plurality of image feature classification results based on the phase identifier so as to select an image feature classification result.

The medical image may comprise a CT, MR or ultrasound image.

An exemplary embodiment may comprise the following main elements:

a first NN layer that is configured to accept multiple-phase images (i.e. multi-phasic images) and the corresponding phase identification numbers as input.

a second NN layer that combines the image features and the phase identification numbers as a vector; and a fully conventional model that receives the combined vector and generates LiRADS features.

According to examples in accordance with an aspect of the invention, there is provided a computer program comprising code means for implementing the method of any preceding claim when said program is run on a processing system.

According to another aspect of the invention, there is provided a processing system for classifying image features of multi-phasic medical images. The system comprises: an interface configured to obtain a medical image and a phase identifier associated with the medical image, the phase identifier representing the phase of the image; and a processing unit configured to combine the medical image and the phase identifier to generate modified image data, to provide the modified image data as an input of a layer of a Neural Network, NN-based learning algorithm configured to classify image features, and to obtain, for the modified image data, an image feature classification result from the NN-based learning.

In some embodiments, the NN-based learning algorithm is trained using a training algorithm configured to receive an array of training inputs and known outputs, wherein the training inputs comprise medical image, medical image segments or medical image features, and wherein the known outputs comprise image feature classifications.

There is also proposed a lesion classification system, comprising the system described above and a user interface configured to receive, from the processing system, and display the image feature classification result.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 3 is an illustration depicting a phase identifier "i" being concatenated to an original medical image as an extract channel;

4

Figure 6:
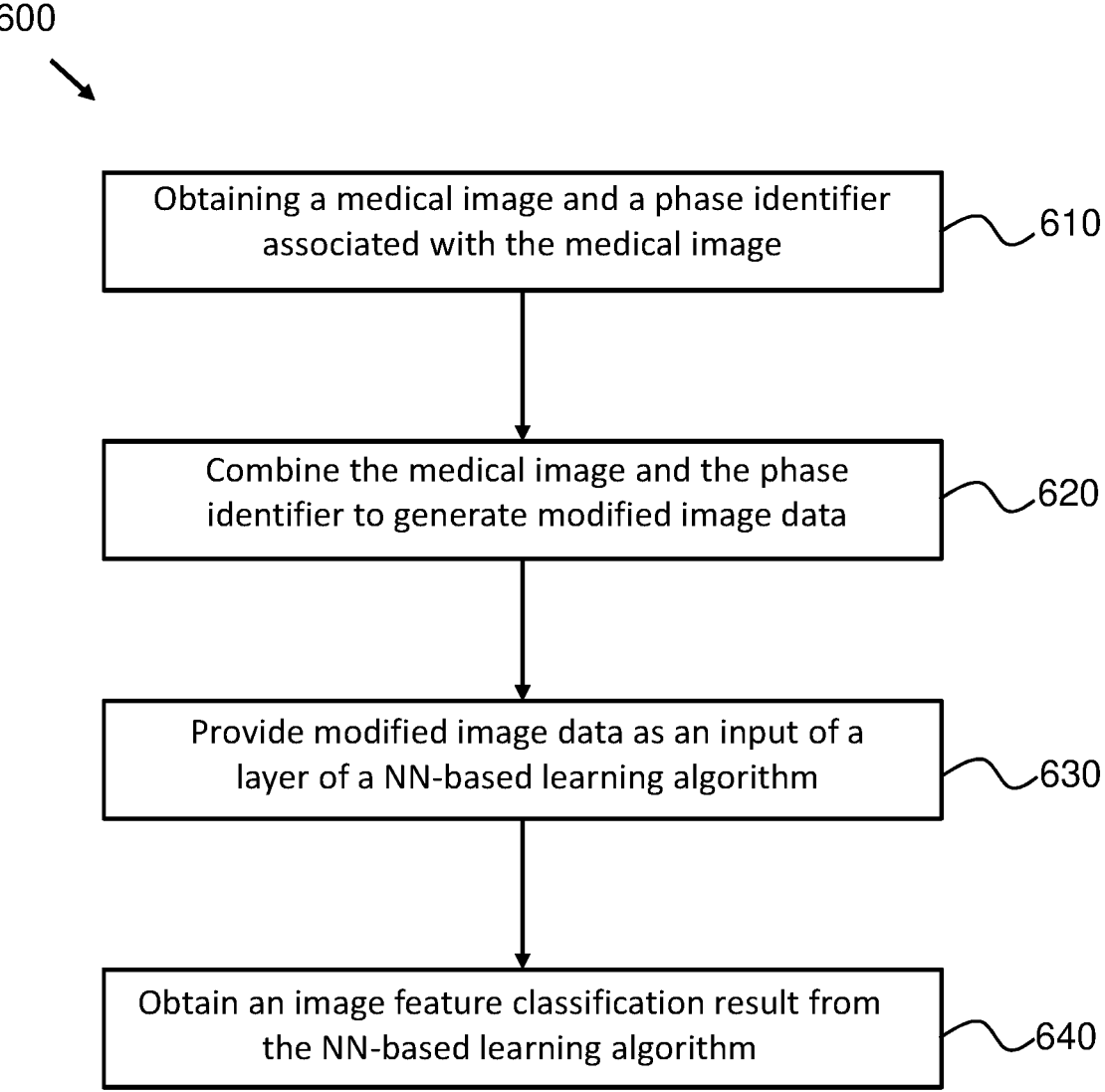
FIG. 6 is a flow diagram of a computer-implemented method for classifying image features of multi-phasic medical images according to an embodiment.

FIG. 7 depicts a modification to the embodiment of FIG. 6.

DETAILED DESCRIPTION OF THE EMBODIMENTS

The invention will be described with reference to the FIGS.

It should be understood that the detailed description and specific examples, while indicating exemplary embodiments of the systems and methods, are intended for the purposes of illustration only and are not intended to limit the scope of the invention. These and other features, aspects and advantages of the systems and methods of the present invention will become better understood from the following description, appended claims and accompanying drawings. It should be understood that the same reference numerals are used throughout the FIGS. to indicate the same or similar parts.

According to a concept of the invention, there is proposed a method and system for classifying image features of multi-phasic medical images. A medical image and a phase identifier associated with the medical image is combined to generate modified image data. The modified image data is provided as an input of a layer of a Neural Network, NN-based learning algorithm configured to classify image features. An image feature classification result from the NN-based learning algorithm is obtained for the modified image data.

Embodiments are at least partly based on the realization image data and phase data may be combined (i.e. mixed together) to provide improved training and classification. In this way, an improved deep NN-based LiRADS feature classifier may be realised.

Illustrative embodiments may, for example, be employed in digital medical imaging platforms as a clinical decision support system. In particular, proposed embodiments may be applicable to liver cancer auto detection systems (especially LiRADS automatic reporting systems).

Figure 1:
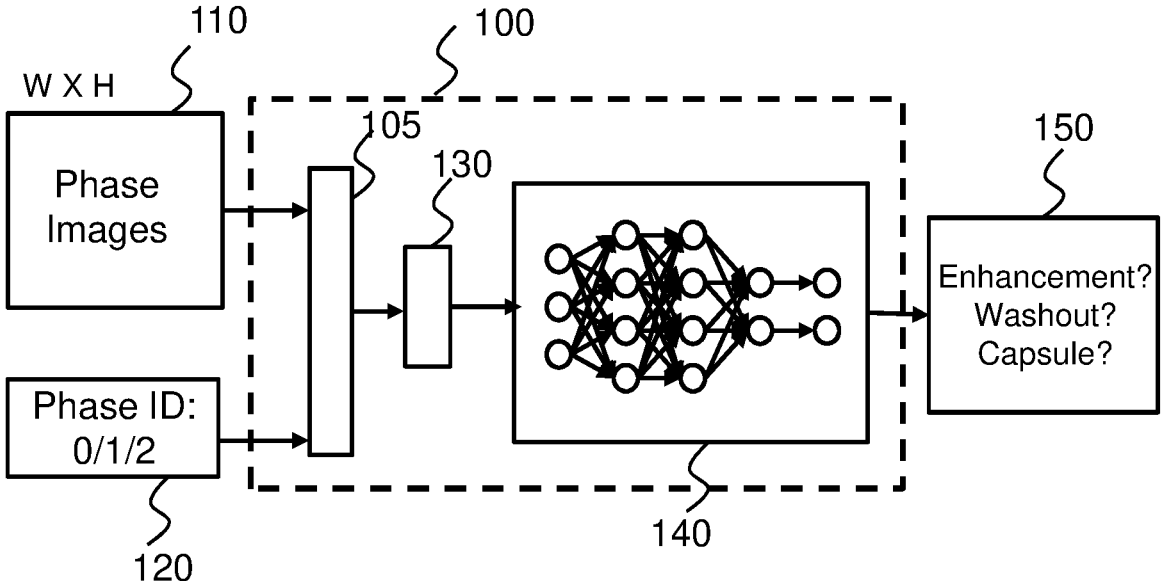
FIG. 1 is a simplified block diagram of a system for classifying image features of multi-phasic medical images according to an exemplary embodiment.

FIG. 1 illustrates a system 100 for classifying image features of multi-phasic medical images according to an exemplary embodiment. The system 100 comprises an interface 105 configured to obtain a multi-phasic medical images 110 and a phase identifier 120 associated with each medical image. Here, a phase identifier is a phase identification number which represents the phase of the associated image (e.g. "0"=arterial phase, "1"=portal venous phase, and "2"=delayed phase).

The system also comprises a processing unit 130 that is configured to combine the medical images and associated phase identifiers to generate modified image data.

The modified image data is provided as an input of a layer of an artificial Neural Network, NN-based learning algorithm 140 of the system. Thus, one or more layers of the NN are adapted to receive multiple-phase images (i.e. multiphasic images) as an input.

The structure of an artificial NN (or, simply, neural network, NN) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

There are several types of neural network, such as convolutional neural networks (CNNs) and recurrent neural networks (RNNs). Embodiments of the present invention employ CNN-based learning algorithms, as CNNs have proved to be particularly successful at analyzing images, and are able to classify images with a much lower error rate than other types of neural network.

CNNs typically contain several layers, including a convolutional layer, a pooling layer, a fully connected layer and a softmax layer. The convolutional layer consists of a set of learnable filters and extracts features from the input. The pooling layer is a form of non-linear down-sampling, reducing the data size by combining the outputs of a plurality of neurons in one layer into a single neuron in the next layer. The fully connected layer connects each neuron in one layer to all the neurons in the next layer. The softmax layer determines a probability distribution for each output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, weightings of the mathematical operation of each neuron may be modified until the error converges. Known methods of modifying a neural network include gradient descent, backpropagation algorithms and so on.

The training input data entries for the NN-based learning algorithm 140 used in the system 100 correspond to example medical images, medical image segments or medical image features. The training output data entries correspond to image feature classifications. Thus, the NN-based learning algorithm 140 is configured to classify image features in accordance with its training.

The images used to train the NN-based learning algorithm 140 may be labeled with three binary numbers to indicate whether there are enhancement, washout, or capsule features. That is, the input training mages each include a lesion and are provides from a lesion segmentation process. The presence of enhancement, washout, or capsule features have been decided from analyzing the output of lesion segmentation process. In this way, the NN-based learning algorithm 140 is trained to decide whether there is enhancement, washout and capsule feature in an image having a detected liver lesion.

Several pre-processing methods may be employed to improve the training sample. For example, images from the same digital imaging system may be normalized in display features such as gamma correction. An image may be segmented using Otsu's method. This region may then be modified into a standard size.

The plurality of NN-based learning algorithms may be produced by modifying existing CNN-based learning algorithms, such as VGG, Inception and ResNet.

From the NN-based learning algorithm 140, an image feature classification result 150 is obtained for the modified image data. For instance, the algorithm 140 predicts if there are enhancement, washout, or capsule features within the input medical images.

Figure 2:
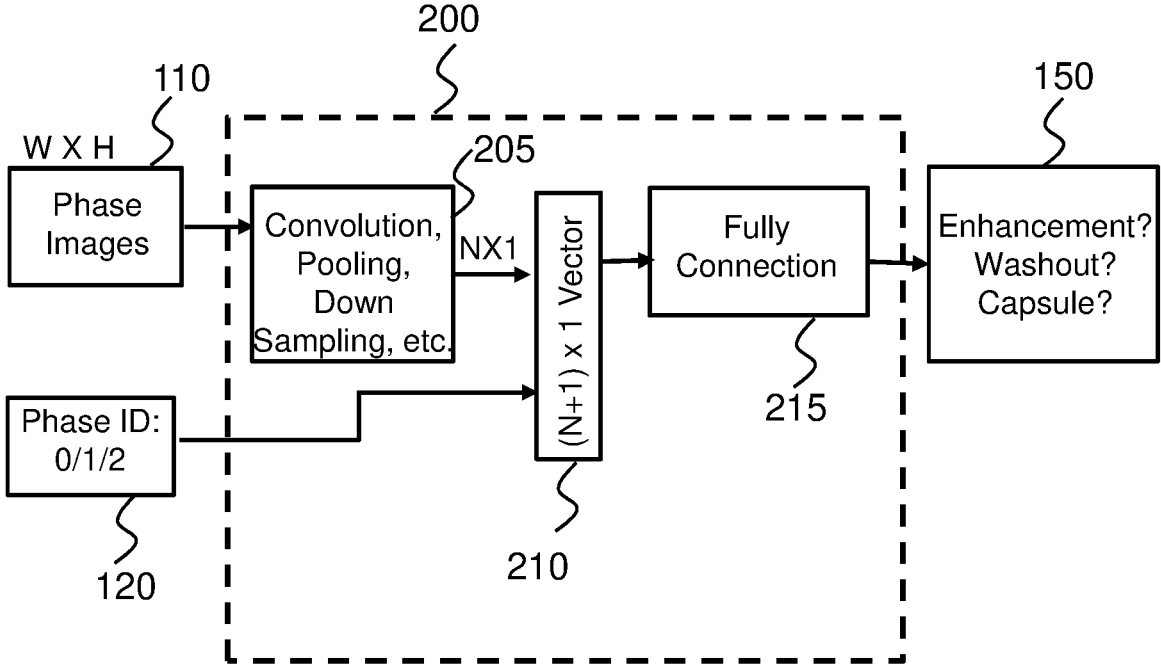
FIG. 2 is there is a simplified block diagram of a system for classifying image features of multi-phasic medical images according to another exemplary embodiment.

Referring now to FIG. 2, there is a depicted a system 200 for classifying image features of multi-phasic medical images according to another embodiment. The embodiment of FIG. 2 differs from that of FIG. 1 in that, in the embodiment of FIG. 2, the phase identifier of an image is combined with the image after the convolution, pooling and down sampling layers, but prior to the fully connected layer.

The inputs to the system 200 are a medical image 110 and its associated phase identification number 120.

The image 100 can be arterial phase, portal venous phase or delayed phase images generated by CT or MR. The image can be the original slice orjust a region of interest (ROI) containing a lesion.

The corresponding phase identification number is "0", "1" or "2" for arterial phase, portal venous phase and delayed phase, respectively, depending on which phase the image belongs to.

Accordingly, in this example of FIG. 2, the input image size is WxH, and the phase number is a scalar number. The input image 110 is first fed into an image feature generation module 205. The image feature generation module consists of a number of NN layers including convolution, pooling, down sampling, batch normalization, activation, etc. It can be any deep learning classifier backbones without the fully connected layer, like the modules in VGG, ResNet, Inception, etc.

The image feature generation module 205 generates a vector with the size as Nx 1. The phase identification number is then combined (by a processor 210) with the image feature vector to generate a new vector with the size (N+1)×1.

This new vector is then provided to the fully connection module 215. The fully connection module 215 generates the prediction(s) 150 whether there is enhancement/washout/ capsule features.

In the exemplary embodiment of FIG. 2, images are labelled with clinical relevance, e.g., arterial enhancement for arterial phase, and washout/capsule only in portal venous/delayed phases. Different phases of images can be mixed together for training and different phases of images can leverage each other to train the image feature generation module 205.

As depicted in FIG. 1, an alternative way to combine (e.g. mix) the phase identifier and the medical image data for a classification model is to combine them at the input side of the NN-based algorithm.

Considering this process of combining a medical image and phase identifier at the input side, it is noted that various different approaches may be employed.

Figure 3:
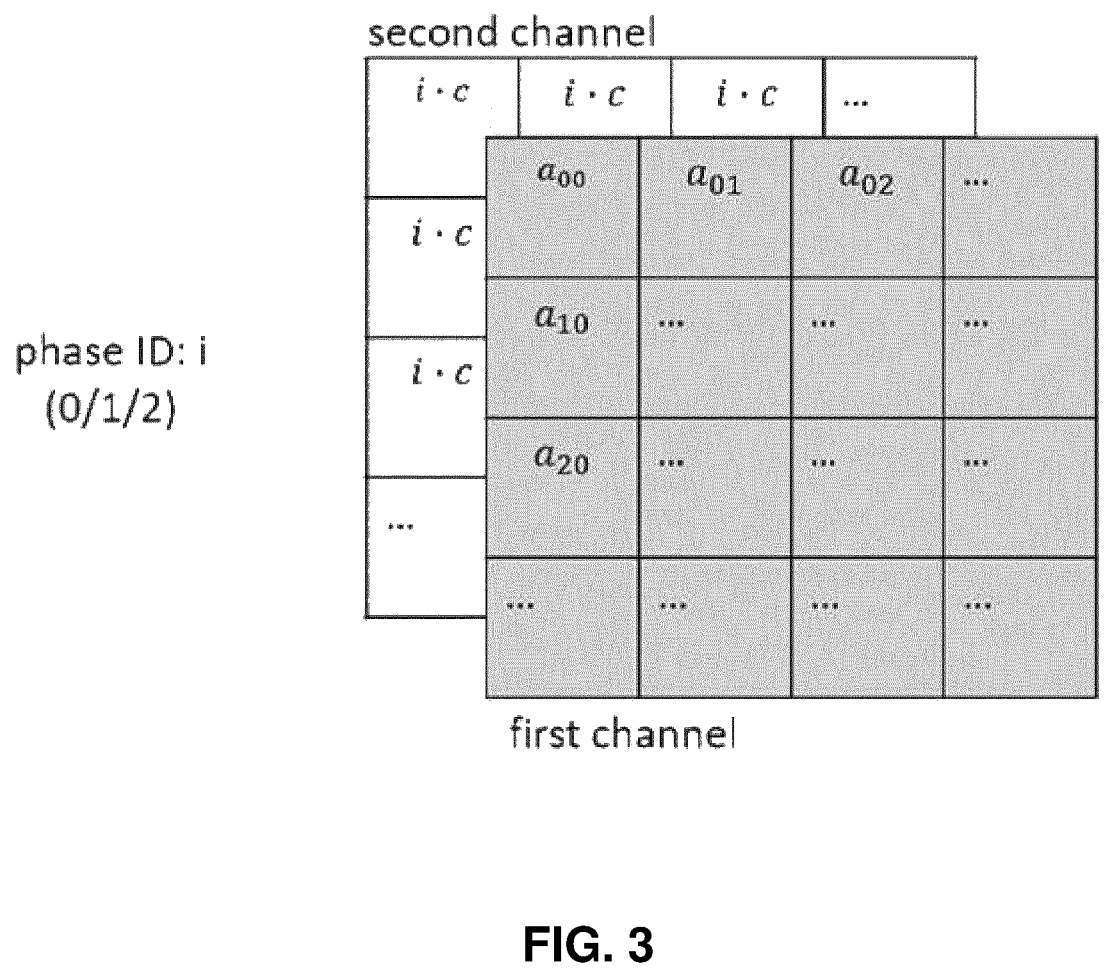

For example, if the phase identifier is a scalar number, it can be concatenated as an extract channel to the image. Such an approach is depicted in FIG. 3 FIG. 3 is an illustration depicting the phase identifier "i" being concatenated to an original medical image as an extract channel. The phase identifier "i" is a scalar number. Specifically, "i" is "0", "1" or "2" for arterial phase, portal venous phase and delayed phase, respectively, depending on which phase the image belongs to. Further, "c" is a constant number employed to balance the value ranges of the original image data and the phase identifier "i".

According to another example, the phase identifier may be combined with its associated medical image by being added to the original image value. Such an approach is depicted in FIG. 4A.

Figure 4A:
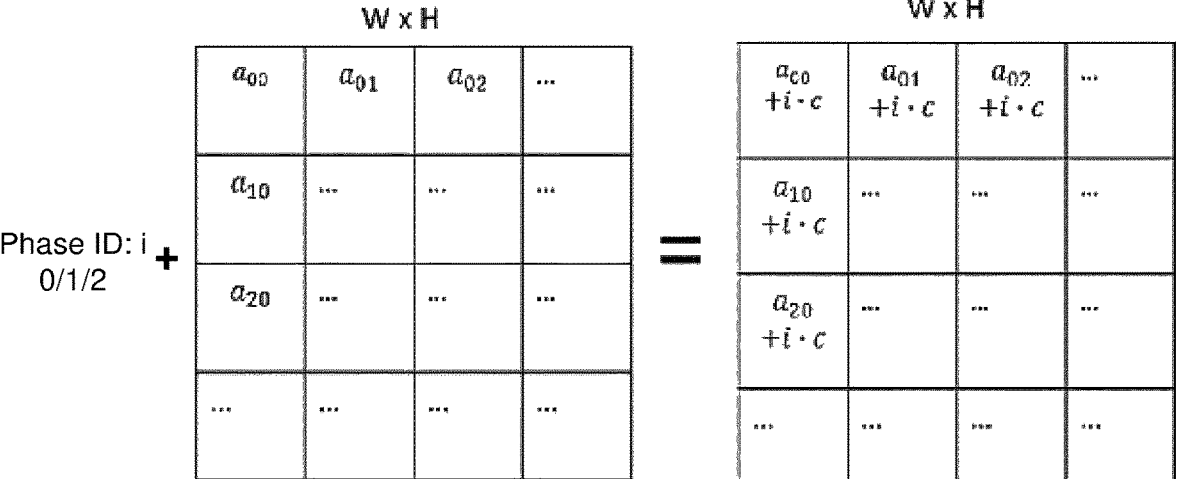
FIG. 4A is an illustration depicting the phase identifier "i" being added to the original image values pixel by pixel, where c is a constant number to balance the value ranges of the original image data and the phase number.

FIG. 4A is an illustration depicting the phase identifier "i" being added to the original image values pixel by pixel, where c is a constant number to balance the value ranges of the original image data and the phase number.

Figure 4B:
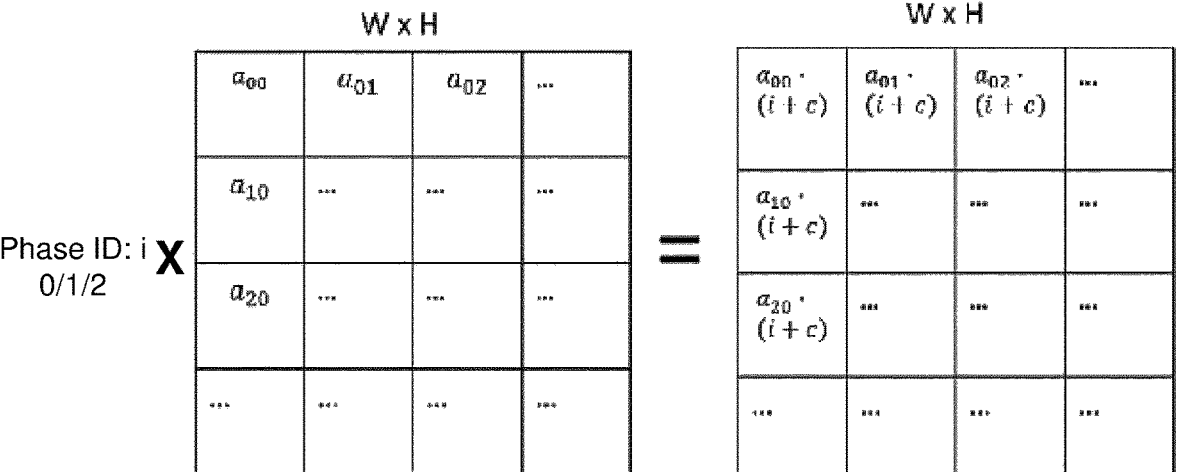
FIG. 4B is an illustration depicting the phase number "i" (plus a constant c) being multiplied to the original image values pixel by pixel.

In another example, the phase identifier may be combined with its associated medical image by being multiplied with the original image value. Such an approach is depicted in FIG. 4B. FIG. 4B is an illustration depicting the phase number "i" plus a constant "c" being multiplied to the original image values pixel by pixel. Here, c is a constant number for balancing the value ranges of the original image data and the phase number.

Figure 5:
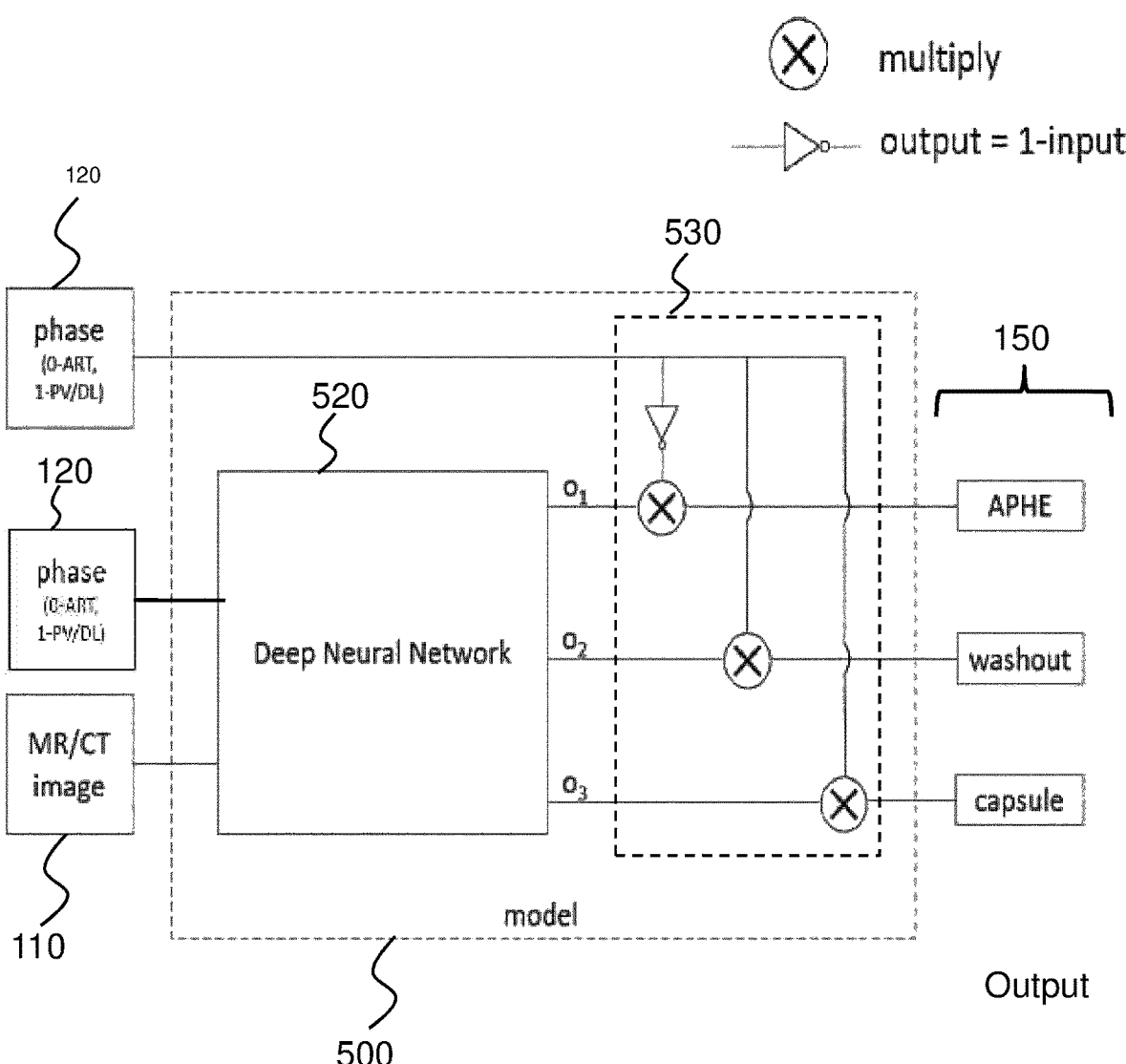
FIG. 5 depicts a system according to another exemplary embodiment.

FIG. 5 depicts a system 500 according to another exemplary embodiment. In particular, the system 500 of FIG. 5 is a modified version of the embodiment of FIG. 1, wherein phase information is further used to implement three switches. In this way, phase information is: (i) added to the image to generate modified image data; and (ii) added as switch information to generate a final result.

The system comprise a deep NN-based classifier 520 which has three binary outputs as o1, o2 and o3 (for enhancement (APHE), washout, and capsule features, respectively).

The input of the NN 520 is a greyscale CT or MR image 110 which contains the liver lesion and a phase identifier 120 associated with the image 110. The image 110 can be from arterial, portal venous or delayed phase. The phase of the image 110 is indicated by the associated phase identifier 120 in the form of binary phase information. The binary phase information is also employed to implement as three switches 530 to control the output of the NN 520. For the phase variable, value "0" identifies that the input greyscale image is from arterial phase, and value "1" identifies that the input greyscale image is from portal venous or delayed phase.

The phase identifier is reversed and multiplied with o1 of the NN 520 to provide the final binary output to indicate whether there is enhancement (APHE) feature. Here, reversed means the phase variable is subtracted from '1.

The phase identified is also multiplied with o2 and o3 of the NN 520, to provide two binary outputs to indicate whether there are washout and capsule features, respectively.

During training of the NN 520, the phase information can select the relevant training error being propagated to the previous layers and switch off the irrelevant training error (e.g. enhancement feature error for portal venous phase image) back propagating. That is, the use of the phase information to implement switches provides the technical effect of controlling error propagation.

According to the proposed concepts and/or embodiments described, one or more of the following advantages may be provided:

(i) Different images from different phases may share the same NN, thus enabling the different images to be leveraged for improved learning;

(ii) Phase information may be considered in the NN-based algorithm, improving prediction; and (iii) During training, any difficulty normally associated with labelling the dataset may be reduced. For instance, although washout and capsule features are only meaningful for portal venous and delayed phase images, for an arterial phase image, the washout and capsule labels don't have any impact on the model (since the branches from o2 and o3 to their respective outputs are switched off and the gradient cannot be further back propagated to the other layers).

By way of yet further example of the proposed concept(s), FIG. 6 is a flow diagram of a computer-implemented method 600 for classifying image features of multi-phasic medical images according to an embodiment. In this example, the medical images comprise images of at least a portion of a liver containing a lesion (as detected by a separate lesion detection process for example).

The method begins with step 610 of obtaining a medical image and a phase identifier associated with the medical image.

Next, in step 620, the medical image and the phase identifier are combined to generate modified image data. In this exemplary method, combining 620 the medical image and the phase identifier comprises: processing the image with an image feature generation algorithm to generate a tensor representing one or more features of the image; and combining the phase identifier with the tensor to generate, as the modified image data, a modified tensor.

Step 630 then comprises providing the modified image data (i.e. the modified tensor) as an input of a hidden layer of a NN-based learning algorithm configured to classify image features. Here, the NN-based learning algorithm comprises a Liver Imaging Reporting and Data System, LI-RADS, feature classifier that is trained to make a decision about the classification of an image feature.

An image feature classification result is then obtained from the NN-based learning algorithm in step 640.

It will be understood that variations may be made to the method depicted in FIG. 6. For example, as described with reference to the embodiment of FIG. 5, embodiments may include switching between classification results based on the phase information. By way of illustration, FIG. 7 depicts such a modified embodiment, wherein the method is similar to that of FIG. 6, but includes the additional step 750 of switching between classification results based on the phase information so as to generate a final result.

It will also be understood that the disclosed methods are computer-implemented methods. As such, there is also proposed a concept of a computer program comprising code means for implementing any described method when said program is run on a processing system.

The skilled person would be readily capable of developing a processor for carrying out any herein described method. Thus, each step of a flow chart may represent a different action performed by a processor, and may be performed by a respective module of the processing processor.

As discussed above, a proposed system may make use of a processor to perform data processing. The processor can be implemented in numerous ways, with software and/or hardware, to perform the various functions required. The processor typically employs one or more microprocessors that may be programmed using software (e.g. microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted that the term "adapted to" is intended to be equivalent to the term "configured to". Any reference signs in the claims should not be construed as limiting the scope.

The invention claimed is:

1. A computer-implemented method for classifying image features of multi-phasic medical images, the computer-implemented method comprising:
   obtaining a medical image and a phase identifier associated with the medical image, the phase identifier representing a phase of the medical image;
   combining the medical image and the phase identifier to generate modified image data;
   providing the modified image data as an input of a layer of a Neural Network (NN)-based learning algorithm configured to classify image features; and
   obtaining, for the modified image data, an image feature classification result from the NN-based learning algorithm;
   wherein combining the medical image and the phase identifier comprises:
      processing the medical image with an image feature generation algorithm to generate a tensor representing one or more features of the medical image; and
      combining the phase identifier with the tensor to generate, as the modified image data, a modified tensor, and
   wherein the phase identifier comprises a numerical value.

2. The computer-implemented method of claim 1, wherein the medical image comprises an image of at least a portion of a liver having a lesion, and wherein the NN-based learning algorithm comprises a Liver Imaging Reporting and Data System feature classifier trained to make a decision about a classification of an image feature.

3. The computer-implemented method of claim 1, wherein the NN-based learning algorithm is trained using a training algorithm configured to receive an array of training inputs and known outputs, wherein the training inputs comprise medical image, medical image segments or medical image features, and wherein the known outputs comprise image feature classifications.

4. The computer-implemented method of claim 1, wherein providing the modified image data to the layer of the NN-based learning algorithm comprises:

providing the modified tensor to a hidden layer trained to make a decision about a classification of an image feature.

5. The computer-implemented method of claim 4, wherein the hidden layer of the NN-based learning algorithm includes a convolution layer or a fully connection layer.

6. The computer-implemented method of claim 5, wherein modifying data of the medical image comprises concatenating the phase identifier to the medical image as an extract channel.

7. The computer-implemented method of claim 5, wherein modifying data of the medical image comprises at least one of:
   adding the numerical value of the phase identifier to pixel values of the medical image; and
   multiplying pixel values of the medical image by the numerical value of the phase identifier.

8. The computer-implemented method of claim 1, wherein combining the medical image and the phase identifier comprises:
   modifying data of the medical image based on the phase identifier to generate the modified image data.

9. The computer-implemented method of claim 1, wherein obtaining, for the modified image data, the image feature classification result from the NN-based learning algorithm comprises:
   obtaining a plurality of image feature classification results from the NN-based learning algorithm; and
   switching between the plurality of image feature classification results based on the phase identifier so as to select the image feature classification result.

10. A non-transitory computer readable medium storing instructions that, when executed by one or more processors, cause the one or more processors to:
   obtain a medical image and a phase identifier associated with the medical image, the phase identifier representing a phase of the medical image;
   combine the medical image and the phase identifier to generate modified image data;
   provide the modified image data as an input of a layer of a Neural Network (NN)-based learning algorithm configured to classify image features; and
   obtain, for the modified image data, an image feature classification result from the NN-based learning algorithm;
   wherein, to combine the medical image and the phase identifier, the instructions, when executed by the one or more processors, further cause the one or more processors to:
      process the medical image with an image feature generation algorithm to generate a tensor representing one or more features of the medical image; and
      combine the phase identifier with the tensor to generate, as the modified image data, a modified tensor, and
   wherein the phase identifier comprises a numerical value.

11. The non-transitory computer readable medium of claim 10, wherein the NN-based learning algorithm is trained using a training algorithm configured to receive an array of training inputs and known outputs, wherein the training inputs comprise medical image, medical image segments or medical image features, and wherein the known outputs comprise image feature classifications.

12. The non-transitory computer readable medium of claim 10, wherein providing the modified image data to a layer of the NN-based learning algorithm comprises:

providing the modified tensor to a hidden layer of the NN-based learning algorithm trained to make a decision about a classification of an image feature.

13. The non-transitory computer readable medium of claim 10, wherein combining the medical image and the phase identifier comprises:

modifying data of the medical image based on the phase identifier to generate the modified image data.

14. The non-transitory computer readable medium of claim 10, wherein modifying data of the medical image comprises at least one of:

adding the numerical value of the phase identifier to pixel values of the medical image; and multiplying pixel values of the medical image by the numerical value of the phase identifier.

15. The non-transitory computer readable medium of claim 10, wherein obtaining, for the modified image data, the image feature classification result from the NN-based learning algorithm comprises:

obtaining a plurality of image feature classification results from the NN-based learning algorithm; and switching between the plurality of image feature classification results based on the phase identifier so as to select the image feature classification result.

16. A system for classifying image features of multiphasic medical images, the system comprising:

a processor configured to:

obtain a medical image and a phase identifier associated with the medical image, the phase identifier representing a phase of the image, combine the medical image and the phase identifier to generate modified image data, provide the modified image data as an input of a layer of a Neural Network (NN)-based learning algorithm configured to classify image features, and obtain, for the modified image data, an image feature classification result from the NN-based learning algorithm, wherein, to combine the medical image and the phase identifier, the processor is further configured to:

process the medical image with an image feature generation algorithm to generate a tensor representing one or more features of the medical image; and combine the phase identifier with the tensor to generate, as the modified image tensor, a modified tensor, and wherein the phase identifier comprises a numerical value.

17. The system of claim 16, wherein the NN-based learning algorithm is trained using a training algorithm configured to receive an array of training inputs and known outputs, wherein the training inputs comprise medical image, medical image segments or medical image features, and wherein the known outputs comprise image feature classifications.

18. The system of claim 16, wherein providing the modified image data to a layer of the NN-based learning algorithm comprises:

providing the modified tensor to a hidden layer of the NN-based learning algorithm trained to make a decision about a classification of an image feature.

19. The system of claim 16, wherein combining the medical image and the phase identifier comprises:

modifying data of the medical image based on the phase identifier to generate the modified image data.

20. The system of claim 16, further comprising:

a user interface configured to receive, from the processor, and display the image feature classification result.

* * * * *